United States Patent [19]

Cavalla et al.

[11] Patent Number: 6,057,445

[45] Date of Patent: May 2, 2000

[54] PURINE COMPOUNDS HAVING PDE IV INHIBITORY ACTIVITY AND METHODS OF SYNTHESIS

[75] Inventors: David J. Cavalla, Cambridge, United Kingdom; Mark Chasin, Manalapan, N.J.; Peter Hofer, Liestal, Switzerland

[73] Assignee: Euro-Celtique S.A., Luxembourg

[21] Appl. No.: 09/209,664

[22] Filed: Dec. 10, 1998

Related U.S. Application Data

[60] Provisional application No. 60/069,371, Dec. 12, 1997.

[51] Int. Cl.[7] .................. C07D 473/34; C07D 471/04; C07D 239/46; C07D 213/75

[52] U.S. Cl. .................. 544/277; 544/314; 546/118; 546/297

[58] Field of Search .................. 544/277; 546/118

[56] References Cited

PUBLICATIONS

Rasmussen, Aus J. Chem 33, 535, 1982.
Er–Rhaimini, Tet. Letters 31, 5757, 1990.
Some New N–Methylpurines, Gertrude B. Elion, CIBA foundation Symp. Chem Biol. Purines, 1957, pp. 39–49.
Selective Type IV Phosphodiesterase Inhibitors as Antiasthmatic Agents. The Syntheses and Biological Activities of 3–(Cyclopentyloxy)–4–methoxybenzamides and Analogues, Michael J. Ashton, et al., Journal of Medicinal Chemistry, 1994, vol. 37, No. 11, pp. 1696–1703.
Synthesis of 3–Methylisoguanine [6–Amino–3–methylpurin–2(3H)–one], G.T. Rogers and T.L. B. Ulbricht, J. Chemical Soc.(C), 1971, pp. 2364–2366.
Synthesis of Potential Anticancer Agents. XIX. 2–Substituted $N^6$–Alkyladenines, John A. Montgomery, Lee B. Holum and Thomas P. JohnstonThe Kettering–Meyer Laboratory, Southern Research Institute, Aug. 5, 1959, vol. S. pp. 3963–3967.
The photosolvolysis of N–arylmethyladenines. Photoremovable N–arylmethyl protective groups for N–containing compounds., A. Er–Rhaimini, et al., Tetrahedron Letters, vol 31, No. 40, pp. 5757–5760, 1990.
Heterocyclic Ambident Nucleophiles. IV* The Alkylation of Metal Salts of Adenine, Malcolm Rasmussen, et al., Aust. J. Chem, 1982, 35, 535–42.

*Primary Examiner*—Mark L. Berch
*Attorney, Agent, or Firm*—Davidson, Davidson & Kappel, LLC

[57] ABSTRACT

The present invention comprises methods of synthesizing compounds having the formula I:

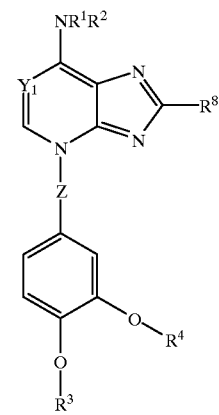

(I)

wherein:
$Y_1$, Z, $R^1$, $R^2$, $R^3$, $R^4$ and $R^8$ are as described herein, which comprises the steps of
(a) reacting a compound of the formula III

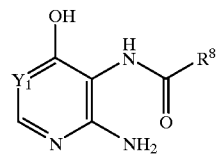

(III)

with a base to cause cyclization to compound IV

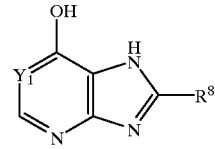

(IV)

(b) transforming said hydroxy group of said compound IV to an amine by successive halogenation by a halogenating agent and displacement of the resultant halogen with an amide to form compound V

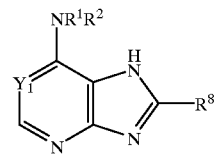

(V)

(c) reacting said compound V with an effective amount of compound VI

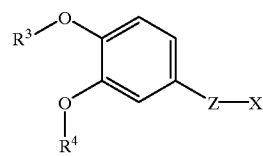

(VI)

to form the compound of formula 1.

19 Claims, No Drawings

PURINE COMPOUNDS HAVING PDE IV INHIBITORY ACTIVITY AND METHODS OF SYNTHESIS

This application is a continuation-in-part of provisional application Ser. No. 60/069,371, filed Dec. 12, 1997.

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these may actually contribute to its activity, only PDE inhibition may account for both the anti-inflammatory and bronchodilatory components. However, theophylline is known to have a narrow therapeutic index and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-monophosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterase Inhibitors For The Therapy Of Asthma", Drug News & Prospectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is cAMP specific, and its inhibition causes airway relaxation, antiinflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula (A):

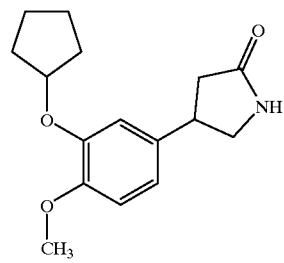

and of RO-20-1724, which has the following structural formula (B):

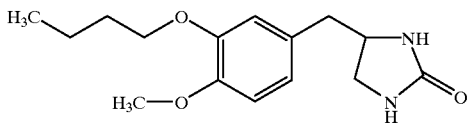

have been studied.

U.S. Pat. No. 4,308,278 discloses compounds of the formula (C)

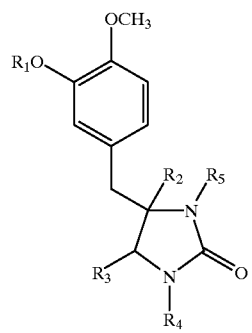

wherein $R_1$ is ($C_3$–$C_6$) cycloalkyl or benzyl; each of $R_2$ and $R_3$ is hydrogen or ($C_1$–$C_4$) alkyl; $R_4$ is $R_2$ or alkoxycarbonyl; and $R_5$ is hydrogen or alkoxycarbonyl.

Compounds of Formula (D) are disclosed in U.S. Pat. No. 3,636,039. These compounds are benzylimidazolidinones which act as hypertensive agents.

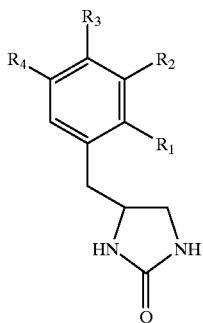

Substituents $R_1$–$R_4$ in Formula D represent a variety of groups, including hydrogen and lower alkyl PCT publication WO 87/06576 discloses antidepressants of Formula E:

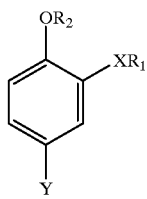

wherein $R_1$ is a polycycloalkyl group having from 7 to 11 carbon atoms; $R_2$ is methyl or ethyl; X is O or NH; and Y comprises a mono- or bicyclic heterocyclic group with optional substituents.

Rolipram, which was initially studied because of its activity as an anti-depressant, has been shown to selectively inhibit the PDE IV enzyme and this compound has since become a standard agent in the classification of PDE enzyme subtypes. There appears to be considerable therapeutic potential for PDE IV inhibitors. Early work focused on depression as a CNS therapeutic endpoint and on inflammation, and has subsequently been extended to include related diseases such as dementia, including vascular dementia, multi-in-farct dementia and Alzheimer's Disease, and asthma. In-vitro, rolipram, RO20-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV is present in all the major inflammatory cells in asthma including eosinophils, neutrophils, T-lymphocytes, macrophages and endothelial cells. Its inhibition causes down regulation of inflammatory cell activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent.

The increased incidence of morbidity and mortality due to asthma in many Western countries over the last decade has focused the clinical emphasis on the inflammatory nature of this disease and the benefit of inhaled steroids. Development of an agent that possesses both bronchodilatory and antiinflammatory properties would be most advantageous.

It appears that selective PDE IV inhibitors should be more effective with fewer side effects than theophylline. Clinical support has been shown for this hypothesis. Furthermore, it would be desirable to provide PDE IV inhibitors which are more potent and selective than rolipram and therefore have a lower $IC_{50}$ so as to reduce the amount of the agent required to effect PDE IV inhibition.

In recent years, several different compounds have been suggested as possible therapeutic compositions which achieve the desired PDE IV inhibition without the side effects alluded to above. However, these efforts have been chiefly directed to developing non-specific derivatives of particular classes of compounds, i.e. rolipram analogs, benzoxazoles, adenines, thioxanthines, etc. These efforts, however, have resulted in a myriad of compounds having a wide range of PDE IV $IC_{50}$'s. Often, the general formulas disclosed yield several compounds which have poor levels of PDE IV inhibition and/or lack sufficient specificity. Consequently, these efforts often provide no assurance that any particular derivative within the formula will have the desired combination of high PDE IV inhibition and selectivity.

It has now been discovered that a variety of fused heterocyclic ring structures having a 3-cyclopentyloxy-4-methoxybenzyl substituent show PDE IV inhibitory activity.

OBJECTS AND SUMMARY OF THE INVENTION

It is accordingly a primary object of the present invention to provide new compounds which are more effective selective PDE IV inhibitors than known prior art compounds.

It is another object of the present invention to provide new compounds which act as effective PDE IV inhibitors with lower PDE III inhibition.

It is another object of the present invention to provide methods for treating a patient requiring PDE IV inhibition.

It is another object of the present invention to provide new compounds for treating disease states associated with abnormally high physiological levels of inflammatory cytokines, including tumor necrosis factor.

It is another object of the present invention to provide a method of synthesizing the new compounds of this invention.

It is another object of the present invention to provide a method for treating a patient suffering from disease states such as asthma, allergies, inflammation, depression, dementia, including vascular dementia, multi-in-farct dementia, and Alzheimer's Disease, a disease caused by Human Immunodeficiency Virus and disease states associated with abnormally high physiological levels of inflammatory cytokines.

Other objects and advantages of the present invention will become apparent from the following detailed description thereof.

With the above and other objects in view, the present invention comprises compounds having the general formula I:

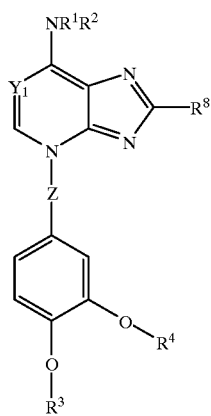

wherein:

$Y_1$ is N or CH;

Z is selected from the group consisting of alkylene groups such as $CH_2$, $CH_2CH_2$, $CH(CH_3)$; alkenylene groups such as CH=CH; alkynylene groups such as C≡C; and NH, N($C_1$–$C_3$ alkyl), O, S, C(O)$CH_2$ and $OCH_2$;

$R^1$ and $R^2$ are independently selected from the group consisting of hydrogen and a $C_1$–$C_8$ straight or branched alkyl or $C_3$–$C_8$ cycloalkyl;

$R^3$ is a $C_1$–$C_{12}$ straight or branched alkyl;

$R^4$ is a $C_3$–$C_{10}$ cycloalkyl optionally substituted with OH, or a $C_3$–$C_{10}$ cycloalkenyl optionally substituted with OH, and $R^8$ is a $C_1$–$C_8$ straight or branched alkyl or a $C_3$–$C_8$ cycloalkyl, optionally substituted with OH.

The present invention is also related to methods of using compounds of formula I for treating patients who can benefit from a modification of PDE IV enzyme activities in their bodies.

The invention also comprises methods of making compounds of formula I, according to a synthetic scheme as generally set forth in Scheme 1. The stated conditions in Scheme 1 are includes as examples only, and are not meant to be limiting in any manner.

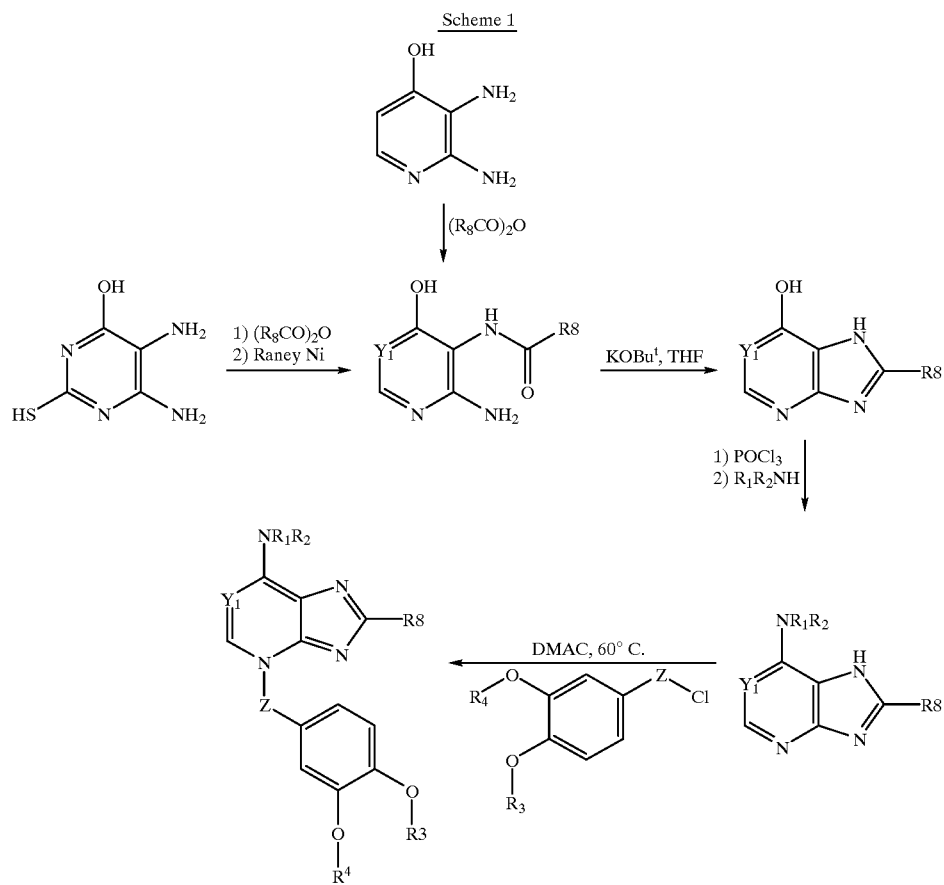

The invention is also related to a method of treating mammals with the above compounds.

DETAILED DESCRIPTION OF THE INVENTION

The present invention is directed to compounds having the general formula I:

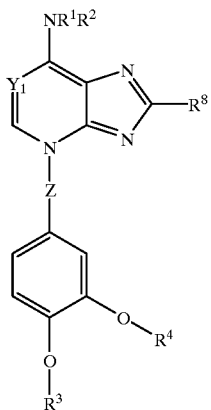

wherein:

$Y_1$ is N or CH;

Z is selected from the group consisting of alkylene groups such as $CH_2$, $CH_2CH_2$, $CH(CH_3)$, alkenylene groups such as $CH=CH$; alkynylene groups such as $C\equiv C$; and NH, $N(C_1-C_3$ alkyl), O, S, $C(O)CH_2$ and $OCH_2$;

$R^1$ and $R^2$ are independently selected from the group consisting of hydrogen and a $C_1-C_8$ straight or branched alkyl or $C_3-C_8$ cycloalkyl;

$R^3$ is a $C_1-C_{12}$ straight or branched alkyl;

$R^4$ is a $C_3-C_{10}$ cycloalkyl optionally substituted with OH, or a $C_3-C_{10}$ cylcoalkenyl optionally substituted with OH; and $R^8$ is a $C_1-C_8$ straight or branched alkyl or a $C_3-C_8$ cycloalkyl, optionally substituted with OH.

As used herein, the following terms are intended to have the meaning as understood by persons of ordinary skill in the art, and are specifically intended to include the meanings set forth below:

"Alkyl" means a linear or branched aliphatic hydrocarbon group having a single radical. Examples of alkyl groups include methyl, propyl, isopropyl, butyl, n-butyl, isobutyl, sec-butyl, tert-butyl, pentyl, hexyl, heptyl, cetyl, and the like. A branched alkyl means that one or more alkyl groups such as methyl, ethyl or propyl are attached to a linear alkyl chain.

The term "cycloalkyl" means a non-aromatic mono- or multicyclic ring system having a single radical. Exemplary monocyclic cycloalkyl rings include cyclopentyl, cyclohexyl and cycloheptyl. Exemplary multicylic cycloalkyl rings include adamantyl and norbornyl.

The term "cycloalkenyl" means a non-aromatic monocyclic or multicyclic ring system containing a carbon-carbon double bond and having a single radical. Exemplary monocyclic cycloalkenyl rings include cyclopentenyl, cyclohexenyl or cycloheptenyl. An exemplary multicyclic cycloalkenyl ring is norbornenyl.

"Alkylene" means a linear or branched aliphatic hydrocarbon group having two radicals. Examples of alkylene groups include methylene, propylene, isopropylene, butylene, and the like.

The term "alkenylene" means a linear or branched aliphatic hydrocarbon group containing a carbon-carbon double bond, having two radicals.

The term "alkynylene" means a linear or branched aliphatic hydrocarbon group containing a carbon-carbon triple bond and, having two radicals.

"Alkoxy" means an alkyl-O-group in which the alkyl group is as previously described. Exemplary alkoxy groups include methoxy, ethoxy, n-propoxy, i-propoxy, n-butoxy and heptoxy.

The term "cycloalkoxy" means a cycloalkyl-O-group in which the cycloalkyl group is as previously described. Exemplary cycloalkoxy groups include cyclopentyloxy.

As used herein, the term "patient" includes both human and other mammals.

The present invention also includes organic and inorganic salts, hydrates, esters, prodrugs and metabolites of the compounds of formula I.

The compounds of the present invention can be administered to anyone requiring PDE IV inhibition. Administration may be orally, topically, by suppository, inhalation or insufflation, or parenterally.

The present invention also encompasses all pharmaceutically acceptable salts of the foregoing compounds. One skilled in the art will recognize that acid addition salts of the presently claimed compounds may be prepared by reaction of the compounds with the appropriate acid via a variety of known methods. Alternatively, alkali and alkaline earth metal salts are prepared by reaction of the compounds of the invention with the appropriate base via a variety of known methods. For example, the sodium salt of the compounds of the invention can be prepared via reacting the compound with sodium hydride.

Various oral dosage forms can be used, including such solid forms as tablets, gelcaps, capsules, caplets, granules, lozenges and bulk powders and liquid forms such as emulsions, solutions and suspensions. The compounds of the present invention can be administered alone or can be combined with various pharmaceutically acceptable carriers and excipients known to those skilled in the art, including but not limited to diluents, suspending agents, solubilizers, binders, retardants, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavorings agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used to formulate oral dosage forms, are described in the *Handbook of Pharmaceutical*

*Excipients*, American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553–1593 (1980), incorporated herein by reference. Techniques and composition for making liquid oral dosage forms are described in *Pharmaceutical Dosage Forms: Disperse Systems*, (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

DETAILED DESCRIPTION OF PREFERRED EMBODIMENTS

As used herein, the term "Et" refers to any ethyl group, and the term "Bu" refers to a butyl group. "Bu$^t$" refers to a tertiary butyl group. The term "THF" refers to tetrohydrofuran. The term "DMAC" refers to dimethyl acetate. The term "Ph" refers to a phenyl group. The terms Z; $Y_1$; $R^1$; $R^2$; $R^3$; $R^4$; and $R^8$ refer to the terms as defined in this application.

The synthetic pathway described in Scheme 1 for producing xanthine compounds of FIG. 1 is described as follows:

Step (a) of the synthetic scheme, compound (III) is reacted with a base e.g. sodium or potassium alkoxide or other alkali metal salts (e.g. calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride) to cause cyclization to compound (IV) as shown below:

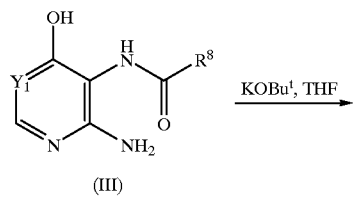

(III)

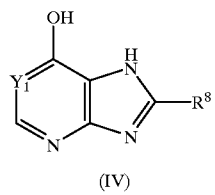

(IV)

The reaction can occur in a suitable solvent e.g. isopropanol or THF.

Step (b) of the synthetic scheme involves the 6-oxo group of compound (IV) being transformed to the amine by successive halogenation (e.g. chlorination) and displacement to give compound (V) of the invention, for example as shown below:

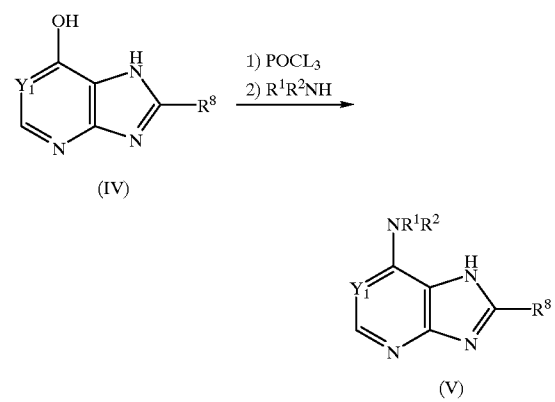

The halogenation step preferably occurs at from about 60° C. to about 120° C., although other temperature ranges can be used, e.g. from about 20° C. to about 150° C. This reaction preferably occurs in a toluene or other hydrocarbon solvent, for example dichloromethane or chloroform, although other solvents may be used. The halogenated intermediate is reacted with an amine to form compound (V) in an alcoholic or aqueous solution at from about 0° C. to about 30° C., although other temperature ranges can be used, e.g. from about 0° C. to about 60° C.

In step (c) of the reaction, compound (V) is reacted with 3-cyclopentyloxy-4-methoxybenzylhalide as shown in compound VI, wherein X is a halogen, preferably chloride, to yield compound (I) of the invention, for example as shown below:

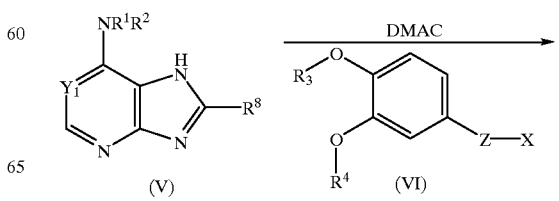

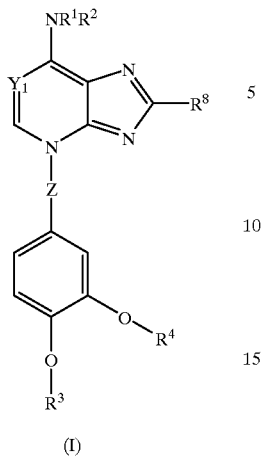

(I)

Step (c) preferably occurs in the presence of DMF or acetonitrile as solvents, although other solvents can be used. This reaction preferably occurs at at a temperature range from about 75° C. to 175° C., although other temperature ranges can be used, e.g. from about 0°0 C. to about 200° C.

In one embodiment of the invention, the compound of formula III is obtained by reacting a pyrimidine compound (IIA) with an acid e.g. an acid anhydride such as isobutyric anhydride or an acid halide; and then a desulfurization compound e.g. rainey nickel or a nickel aluminum alloy to form compound (III), where $Y_1$ is N, for example as depicted below:

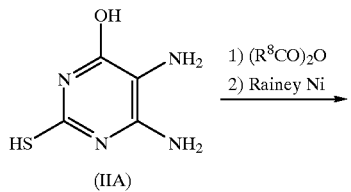

(IIA)

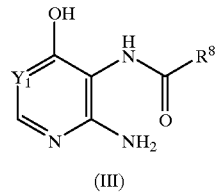

(III)

The acid reaction preferably occurs from about 20° C. to about 80° C., although other temperatures ranges can be used if necessary. This reaction preferably occurs in the presence of acetonitrile ($CH_3CN$), DMF or a combination thereof as solvents, although other suitable solvents can be used.

The subsequent desulfurization reaction preferably occurs from about 20° C. to about 80° C., although other temperatures ranges can be used if necessary. This reaction preferably occurs in the presence of sodium hydroxide solution as a solvent, although other suitable solvents can be used.

Alternatively, a pyridine compound (IIB) is substituted for the pyrimidine compound (IIA) in step (a) to form compound (III), where Y is C, for example as depicted below:

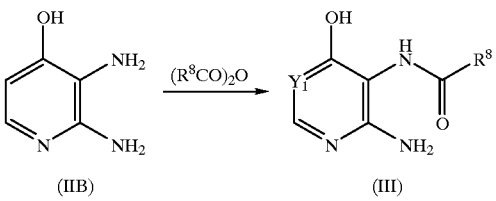

wherein the desulfurization step in not necessary.

In another embodiment of the invention, compounds wherein Z is CH=CH may be obtained from Wittig reactions of the type depicted below in Scheme 2, in which alkenes are formed from carbonyl compounds and phosphonium ylids. The Wittig reactions are likely to yield a mixture of cis and trans forms.

Scheme 2

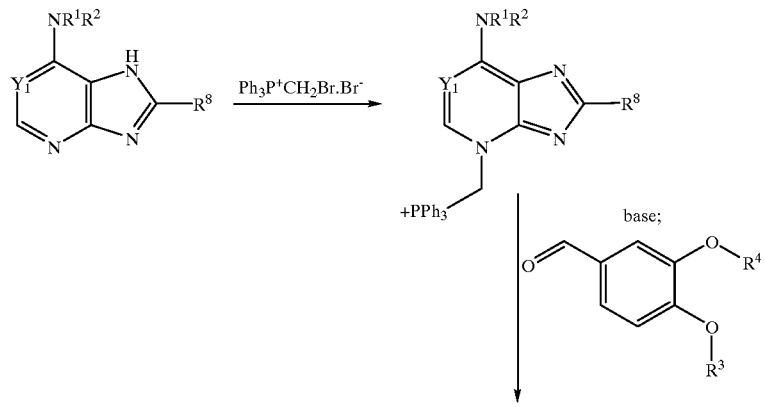

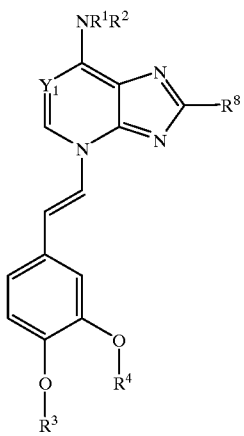

EXAMPLE 1

3-(3-Cyclopentyloxy-4-methoxybenzyl)-6-ethylamino-8-isopropyl-3H-purine

The title compound was prepared by the following synthetic pathway:

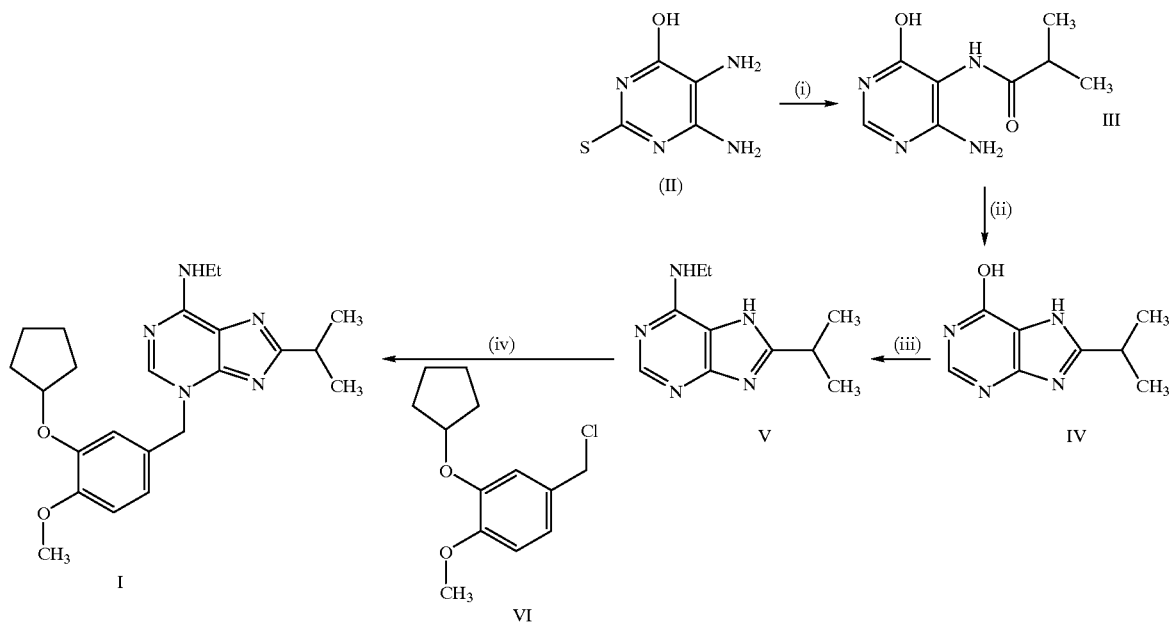

The pathway occured under the conditions set forth in Table 1 below. The pathway can occur under other suitable conditions known in the art and the particular conditions disclosed herein are not meant to be limiting.

| Step | Compound | Conditions | Yield |
|---|---|---|---|
| (i) | (IIA) | (i-PrCO)$_2$O, DMF, MeCN, 60° C. | 79–81% |
|  |  | Ni/Al alloy, NaOH(aq), 50° C., 24 h | 75–87% |
| (ii) | (III) | KOBu$^t$, iPrOH, reflux | 96% |
| (iii) | (IV) | POCl$_3$, 100° C. | 47% |

-continued

| Step | Compound | Conditions | Yield |
|---|---|---|---|
| (iv) | (V) | EtNH$_2$, EtOH DMF, 150° C., Compound VI | 34–60% |

Step (i) Synthesis of 6-amino-4-hydroxy-5-isobutyrylamidopyrimidine 5,6-Diamino-4-hydroxy-2-mercaptopyrimidine (IIA) (Aldrich) (100 g, 0.632 mol) was suspended in a mixture of acetonitrile (600 ml) and N,N-dimethylformamide (200 ml). Isobutyric anhydride (115 ml, 0.693 mol) was added and the mixture heated at 50° C. for 4 h, then allowed to cool to room temperature overnight. Ether (400 ml) was added and the mixture filtered to give an orange solid. This was dissolved in sodium hydroxide (1M) (700 ml) and the pH adjusted to 6.5 using concentrated hydrochloric acid. The mixture was cooled in ice for 30 minutes, filtered, the solid washed with acetone and dried in an oven at 40° C. to give 6-amino-4-hydroxy-5-isobutyrylamido-2-mercaptopyrimidine (81.32 g) m.p 293–294° C. as an orange solid. The aqueous filtrate was left overnight, and the pH adjusted to 6.5 with concentrated hydrochloric acid. The solid was collected by filtration, washed with acetone and dried in an oven at 40° C. to give further 6-amino-4-hydroxy-5-isobutyrylamido-2-mercaptopyrimidine m.p. 286.2–287° C. (33.44 g), combined yield (1 14.76 g, 80%). 6-Amino-4-hydroxy-5-isobutyrylamido-2-mercaptopyrimidine (70 g, 0.307 mol) was dissolved in sodium hydroxide solution 1M (450 ml) with stirring. Nickel aluminium alloy (140 g) was added in small portions (very exothermic and requires ice cooling) and the resulting mixture heated at 50° C. overnight. Tlc (SiO$_2$, MeOH:EtOAc, 1:1) showed some starting material to be still present. Further sodium hydroxide solution 1M (50 ml) and nickel aluminium alloy (25 g) were added (reaction again very exothermic and requires ice cooling to stabilise) and the resulting mixture maintained at 50° C. for a further 4 h at which time Tlc indicated the reaction to be complete. The nickel aluminium alloy was filtered off and the filtrate carefully acidified to pH 6.5 with concentrated hydrochloric acid. The mixture was cooled in ice for 1 h, the solid filtered off washed with ice-cold acetone and dried in vacuo at 40° C. to give the 6-amino-4-hydroxy-5-isobutyrylamidopyrimidine (III) (46.59 g) as a pale yellow solid. The filtrate was concentrated to dryness in vacuo, resuspended in water (2–300 ml), filtered off, washed with ice cold acetone and dried in vacuo at 40° C. to give further 6-amino-4-hydroxy-5-isobutyrylamidopyrimidine (III) (5.54 g) as a pale yellow solid (52.13 g, 74.5%), m.p. 270–272° C. Tlc (SiO$_2$, MeOH:EtOAc, 1:1) Rf 0.69 detection U.V.

Step (ii) 6-hydroxy-8-isopropyl-3H-purine

6-Amino-4-hydroxy-5-isobutyrylamidopyrimidine (26.15 g, 0.133 mol) was suspended in dry isopropanol (500 ml). Potassium-t-butoxide (44.8 g, 0.4 mol) was added and the resulting mixture heated at reflux for 7 h. The cooled mixture was evaporated to dryness in vacuo, the residue dissolved in water (300 ml) and the pH adjusted to 7.0 using concentrated hydrochloric acid. The mixture was cooled in ice, the solid collected by filtration, washed with acetone (200 ml) and dried in vacuo at 40° C. to give 6-hydroxy-8-isopropyl-3H-purine (IV) (17.7 g, 74.5%) as a yellow solid m.p.=346–348° C. (dec). The aqueous filtrate was evaporated to dryness in vacuo, water (100 ml) was added, the solid filtered off, washed with acetone (100 ml) and dried in vacuo at 40° C. to give further 6-hydroxy-8-isopropyl-3H-purine (IV) (5.0 g, 21%) (total yield 96%).

An alternative work up procedure was as follows: the cooled reaction mixture was evaporated to dryness in vacuo, the residue dissolved in water and the pH adjusted to 6.5 with concentrated hydrochloric acid. The mixture was again evaporated to dryness in vacuo, and the residue washed with hot ethanol until tlc (SiO$_2$ eluting with 1:1 MeOH:EtOAc) indicated no product was present in the filtrate. The filtrate was evaporated to dryness in vacuo to give 6-hydroxy-8-isopropyl-3H-purine (IV) as a yellow solid. The hypoxanthine is appreciably soluble in water.

Step (iii) 6-Ethylamino-8-isopropyl-3H-purine

6-Amino-4-chloro-5-isobutyrylamidopyrimidine (4.0 g, 18.7 mmol) and phosphorus oxychloride (30 ml) were heated together at 110° C. for 20 h. The excess phosphorus oxychloride was removed in vacuo, and the residue triturated with ether (4×50 ml) and dried to give the intermediate chloropurine (6.3 g) m.p. 209°–211° C. The chloropurine was dissolved in ethanol (50 ml) and ethylamine (70% solution in water) (20 ml) was added and the solution heated at 70° C. under a nitrogen atmosphere for 24 h. The solvent was removed in vacuo and the residue partitioned between 10% aqueous potassium carbonate solution (100 ml) and dichloromethane:methanol (10:1, 100 ml). The organic phase was separated and the aqueous phase further extracted with dichloromethane:methanol (10:1, 3×100 ml). The combined organics were dried (MgSO$_4$) and evaporated to dryness in vacuo to leave a pale yellow solid (4.2 g). This was recrystallised from toluene (250 ml) to give the title compound (2.88 g, 75%) as a fluffy white crystalline solid m.p.=183–184° C. Tlc (SiO$_2$,ethyl acetate:methanol 10:1), Rf=0.59 detection U.V.

Step (iv) 6-Ethylamino-3-(3-Cyclopentyloxy-4-methoxybenzyl)-8-isopropyl-3H-purine hydrochloride 6-ethylamino-8-isopropyl-3H-purine (7.52 g, 36.65 mmol) and 3-cyclopentyloxy-4-methoxybenzylchloride (10.59 g, 43.98 mmol) were dissolved in acetonitrile (30 ml) in a high pressure vessel and the resulting mixture heated are 120° C. for 24 hours. On cooling to room temperature a solid precipitated from the solution. The solvent was removed in vacuo, cold water (10 ml) and diethyl ether (100 ml) were added to the solid residue, the mixture stirred vigourously and then filtered. The filter cake was washed with ice-cold ethyl acetate (50 ml) and the solid obtained was oven dried in vacuo at 80° C. to give the title compound (9.51 g, 58%) as a slightly off-white solid. The combined filtrates and washings were concentrated in-vacuo, then water (5 ml) and diethyl ether (100 ml) added, and the mixture treated as before to give further title compound (0.718 g, 5%) as a white solid, m.p.=205–207° C. Combined yield 910.23 g, 63%). Tlc, SiO2 (dichloromethane:methanol, 10:1) Rf=0.49, detection U.V., Dragendorff's reagent.

While the invention has been illustrated with respect to the production and use of particular compounds, it is apparent that variations and modifications of the invention can be made without departing from the spirit or scope of the invention.

Having thus described the invention, what is claimed is:

1. A method of forming a compound having the formula I

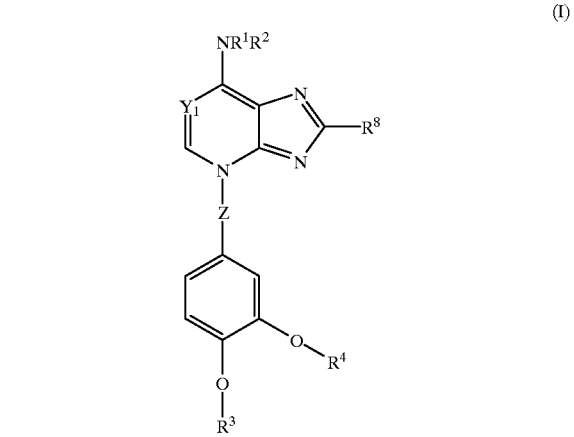

(I)

wherein:

Y$_1$ is N or CH

Z is selected from the group consisting of CH$_2$, CH$_2$CH$_2$, CH(CH$_3$), CH=CH, C≡C, NH, N(C$_1$–C$_3$ alkyl), O, S, C(O)CH$_2$ and OCH$_2$;

$R^1$ and $R^2$ are independently selected from the group consisting of hydrogen and a $C_1$–$C_8$ straight or branched alkyl or a $C_3$–$C_8$ cycloalkyl;

$R^3$ is a $C_1$–$C_{12}$ straight or branched alkyl;

$R^4$ is a $C_3$–$C_{10}$ cycloalkyl optionally substituted with OH, or a $C_3$–$C_{10}$ cycloalkenyl optionally substituted with OH; and $R^8$ is a $C_1$–$C_8$ straight or branched alkyl or a $C_3$–$C_8$ cycloalkyl, optionally substituted with OH;

said method comprising the steps of
(a) reacting a compound of the formula III

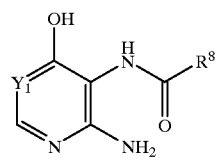

(III)

wherein $Y_1$ and $R^8$ are as defined above, with a base to cause cyclization to compound IV

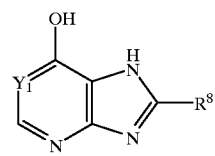

(IV)

wherein $Y_1$ and $R^8$ are as defined above;

(b) transforming said hydroxy group of said compound IV to an amine by successive halogenation by a halogenating agent and displacement of the resultant halogen with an amine group of the formula $NR_1R_2$, wherein $R_1R_2$ are as defined above, to form compound V

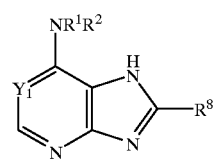

(V)

wherein $R^1$, $R^2$ and $R^8$ are as defined above;

(c) reacting said compound V with an effective amount of compound VI

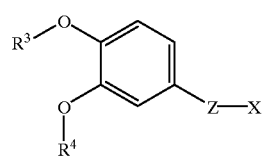

(VI)

wherein $R^3$ and $R^4$ are as defined above and X is a halogen; to form the compound of formula I.

2. The method of claim 1 wherein $R^4$ is cyclopentyl.
3. The method of claim 2 wherein $R^3$ is methyl.
4. The method of claim 3 where Z is $CH_2$.

5. The method of claim 1, wherein said base is an alkali metal salt.

6. The method of claim 1, wherein said alkali metal salt is selected from the group consisting of sodium alkoxide and potassium alkoxide.

7. The method of claim 1, wherein said step (a) occurs in a solvent selected from the group consisting of isopropanol, tetrohydrofuran and mixtures thereof.

8. The method of claim 1, wherein said halogenating agent of step (b) is selected from the group consisting of phosphorous chloride, thionyl chloride and oxalyl chloride.

9. The method of claim 1, wherein said step (c) occurs in N,N-dimethylformamide.

10. The method of claim 1, wherein X is chloride.

11. The method of claim 1, wherein $Y_1$ is N and wherein said compound of formula III is obtained by reacting a compound of the formula IIA

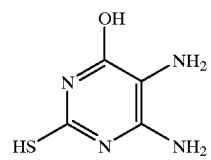

(IIA)

with an effective amount of a compound selected from the group consisting of an acid anhydride having an $R^8C(O)$ moiety or an acid halide having an $R^8C(O)$ moiety; and a desulfurization compound.

12. The method of claim 1, wherein Z is CH=CH and wherein said compound of formula V is reacted with an effective amount of a methyltriphenylphosphoniumbromide to form a compound of the formula VII

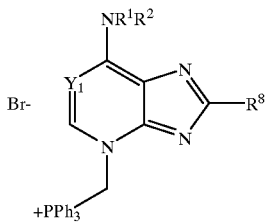

(VII)

wherein $Y_1$, $R^1$, $R^2$ and $R^8$ are as defined above; and reacting said compound VII with an effective amount of compound VIII

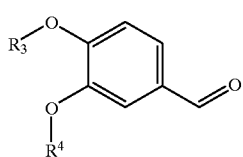

(VIII)

wherein $R^3$ and $R^4$ are as defined above; in the presence of a base to form the compound of formula I.

13. The method of claim 11, wherein said acid anhydride is isobytyric anhydride.

14. The method of claim 10, wherein said desulfurization compound is selected from the group consisting of rainey nickel and a nickel aluminum alloy.

15. The method of claim 10, wherein said step to obtain the compound of formula (III) occurs in a solvent selected from the group consisting of acetonitrile, N,N-dimethylformamide and mixtures thereof.

16. The method of claim 1, wherein $Y_1$ is CH and wherein said compound of formula III is obtained by reacting a compound of the formula IIB

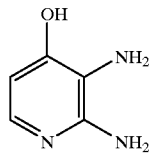

(IIB)

with an effective amount of a compound selected from the group consisting of an acid anhydride having an $R^8C(O)$ moiety or an acid halide having an $R^8C(O)$ moiety.

17. The method of claim 1 wherein said compound of formula I is 3-(3-Cyclopentyloxy-4-methoxybenzyl)-6-ethylamino-8-isopropyl-3H-purine.

18. The method of claim 16, wherein said acid anhydride is isobytyric anhydride.

19. The method of claim 16, wherein said step to obtain the compound of formula (III) occurs in a solvent selected from the group consisting of acetonitrile, N,N-dimethylformamide and mixtures thereof.

* * * * *